United States Patent
van Haeringen et al.

(10) Patent No.: US 6,495,325 B1
(45) Date of Patent: Dec. 17, 2002

(54) DETECTION AND QUANTIFICATION OF MICRO-ORGANISMS USING AMPLIFICATION AND RESTRICTION ENZYME ANALYSIS

(75) Inventors: Hendrick van Haeringen, Veenendaal (NL); Willem Anne van Haeringen, Veenendaal (NL)

(73) Assignee: Dr. van Haeringen Laboratorium B.V., Wageningen (NL)

( * ) Notice: Subject to any disclaimer, the term of this patent is extended or adjusted under 35 U.S.C. 154(b) by 0 days.

(21) Appl. No.: 09/702,561

(22) Filed: Oct. 31, 2000

Related U.S. Application Data

(63) Continuation of application No. PCT/NL00/00125, filed on Mar. 1, 2000.

(30) Foreign Application Priority Data

Mar. 1, 1999 (EP) .............................................. 99200565

(51) Int. Cl.$^7$ ........................... C12Q 1/68; C12P 19/34; C07H 21/04
(52) U.S. Cl. ........................ 435/6; 435/91.2; 536/24.33
(58) Field of Search .................. 435/6, 91.2; 536/24.33

(56) References Cited

U.S. PATENT DOCUMENTS 5,543,294 A * 8/1996 Silverstein et al. ............ 435/6
5,571,674 A * 11/1996 Hoshina et al. ................ 435/6

OTHER PUBLICATIONS

Statagene Catalog.Gene characterization kits. p. 39, 1998.*
Stratagene Catalog. Chameleon double–stranded, site–directed mutagenesis kit. pp. 132–133, 1995.*
Haddad A et al. Phylogenetic characterization of the epibiotic bacteria associated with the hydrothermal vent polychaete Alvinella pompejana. Applied and Environmental Microbiology, vol. 61(5): 1679–1687, 1995.*
Stratagene Catalog. Systems and kits. Stratagene Catalog, p. 132–133, 1995.*
Abstract XP–002123391.
Abstract XP–002123392.
Abstract XP–002123465.
PCT International Search Report, PCT/NL00/00125, dated Aug. 17, 2000, 2 pages.
Ratcliff et al., "Use of gene Amplification to Detect Clostridium Difficile in Clinical Specimens", *Pathology*, 26, pp. 477–479, 1994.

* cited by examiner

Primary Examiner—Jeffrey Fredman
Assistant Examiner—Suryaprabha Chunduru
(74) Attorney, Agent, or Firm—TraskBritt

(57) ABSTRACT

In livestock, a number of pathological conditions and/or syndromes exist which may not be attributable to infection by a single organism. In many instances, these pathological conditions and/or syndromes have an effect on the equilibrium that ordinarily exists within the various bacteria comprising the normal bacterial flora. A number of these pathological conditions and/or syndromes have been clinically referred to as dysbacteriosis and bacterial overgrowth. The present invention provides methods for evaluation of the "general health" of livestock by analyzing the composition of microbiological flora. In one aspect, a method of the invention comprises providing a sample of microbiological flora, selectively amplifying nucleic acid in the flora sample, subjecting the amplificate to restriction digestion, and then analyzing the resulting pattern of restriction fragments.

18 Claims, 4 Drawing Sheets

DETECTION AND QUANTIFICATION OF MICRO-ORGANISMS USING AMPLIFICATION AND RESTRICTION ENZYME ANALYSIS

RELATED APPLICATIONS

This application is a continuation of co-pending International Application No. PCT/NL00/00125, filed Mar. 1, 2000, designating the United States of America, which itself claims priority from EP 99200565.2, filed on Mar. 1, 1999.

TECHNICAL FIELD

The present invention relates to methods and means for diagnosis of pathological or other detrimental conditions affecting the general health of a group of individuals, in particular vertebrates, and more typically mammals and/or birds, such as livestock. The invention further relates to methods and means for microbiological typing of substances comprising a variety of microbiological organisms such as, but not limited to, food, food additives, waste material, soils etc. The invention is exemplified by using feces as a source of microbiological populations. However, the methods and means of the invention are equally applicable to microbiological populations from other sources.

BACKGROUND

In livestock a number of pathological conditions and/or syndromes have been noticed that do not seem attributable to, e.g., an infection with a single micro-organism. These syndromes, however, do seem to have an effect on the equilibrium which normally exists within the different bacteria constituting the bacterial flora. A number of these syndromes are referred to as dysbacteriosis and bacterial overgrowth.

Although not wishing to be bound by theory, a possible explanation for the presence of these syndromes is that these diseases may occur due to:

1. feed intake/feed type.

The feed interferes with the digestion, resulting in changes in the bacteria. Some particular bacteria or groups of bacteria are abundant and overwhelming, some particular bacteria or groups of bacteria are inhibited and cannot survive.

2. Invasion of one (or more) bacterial species.

The bacteria need not be pathogenic themselves, to disturb the balance within the flora.

3. Invasion of one (or more) viral or fungal species,
4. Immune depression,
5. Environmental effects such as temperature and humidity.

Typically, these syndromes do have an influence on the general health and performances of an animal and often even on the whole of the group of animals. In poultry, there are even a number of syndromes which show clinical symptoms directly related to the condition of the intestinal bacterial flora. Therefore, it is of importance to be capable to check the general health of a population of livestock, and/or to have a means of at least determining the presence of such an ill-defined pathological condition in a group (herd, flock) of, e.g., livestock.

Examples of syndromes related to bacterial disequilibrium are, e.g., steathorroea in calves, ileitis in pigs, and also diarrhea at weaning, diarrhea in poultry.

DISCLOSURE OF THE INVENTION

The present invention provides novel means (e.g., kits) and methods for determining (relative) abundance as well as (estimates) of actual amounts of different bacteria present in intestinal bacterial flora, in order to determine, e.g., the presence or absence of equilibrium in said intestinal bacterial flora, especially when compared to a set of normal compositions of intestinal bacterial flora. Until the present invention analyses of bacterial flora occurred with methods used in classical bacteriology. In classical bacteriology, which is based on cultivation and identification of different bacterial strains. Various methods are used, including aerobic and anaerobic growth, pre-enrichment, etc., Furthermore, counting the number of colonies has generally been used to obtain information about the number of bacteria present in samples.

Using these methods, only an estimated 20% of the bacteria have been isolated and characterised until now. Nearly axiomatic in these classical bacterial techniques (as well as with techniques finding other micro-organisms, such as viruses, yeast or fungi) is the thinking that one disease has one causal agent, or at least that one or a distinct few agents can be considered instrumental in causing the distinct disease. However, these classical insights to not provide any practical manner of obtaining insight into the presence or absence of a "healthy" equilibrium in intestinal tracts.

Thus, the present invention provides a method for analysing the composition of microbiological (e.g. viral, fungal, yeast or bacterial) flora in an intestinal tract, comprising providing a sample of said flora, selectively amplifying nucleic acid in said sample, subjecting the amplificate to restriction digestion and analysing the resulting pattern of restriction fragments, and providing detection of interrelationships between flora constituents such as known and unknown bacteria, fungi, viruses and the like, for example under distinct disease conditions without the need to identify an organism. Said nucleic acid is selectively amplified, albeit usually from as many, or the greater part of, micro-organism species as possible present in said sample, and optionally supplemented with specific amplification of known organism species or parts thereof possibly present in said sample to provide optional identification, when so desired. Typical results include the detection of a cluster or clusters of amplified fragments (which may have been subjected to restriction), said fragments localised or detected in a pattern (governed for example by molecular mass) allowing the recognition of specific (cluster) patterns. These may be identical in various samples, may be different, or may be supplemented with additional clusters (typically nearly equally sized fragments). Typically, when the sample is representative of a "normal" population, a well balanced cluster pattern may be seen. In contrast, when dysbacteriosis or overgrowth has occurred, one cluster (commonly representing one micro-organism) may be over-represented, typically to the detriment of other clusters (representing others)

The sample may typically be derived from feces, or a biopsy, and in many cases can be taken post-mortem. Preferably, samples are taken under conditions which can be repeated, so that the differences in the flora are attributable to the conditions to be diagnosed and/or analyzed, and not to factors which are temporal, dietary or the like. Post-mortem samples and biopsies should be taken from the same area in the intestinal tract. When using this technique as provided by the invention, it is not per se the mere identification of a tentative causal micro-organism that matters. Rather as the recognition of distinct patters in the resulting analysis allow determinations of equilibrium with respect to a distinct or fitting condition (diseased or non-diseased) in said flora, and allow identification of similar pattern in animals from the same or different flock. Clearly, classical techniques have not paid attention to patterns in flora that, for example relate to multifactorial disease patterns, but have commonly tried to identify one or more distinct causal agents, which in general are sought after with predetermined and specific detection means, such as nucleic acid primers or probes, antibodies, and so on, for the detection of specific micro-organisms or specific components thereof. For example, U.S. Pat. No. 5,543,294; JP 05 317096; Ratcliff et al., Path. (1994) 26:477–479; Wood et al., Appl. Env. Microb. (1998) 64:3683–3689; and U.S. Pat. No. 5,571,674 all give specific and direct instructions on how to identify a specific bacterium, or a bacterium belonging to a specific genus or family, but do not pay attention to other micro-organisms that are or may be present in the test samples, clearly demonstrating that they are not interested in the whole content of the flora but only in specific micro-organisms therein. They will therefore never be able to detect interrelationships between flora constituents such as known and unknown bacteria, fungi, viruses and the like.

In the field of bacteriology, the invention, for example provides the means for quality control, identification and quantification of bacterial species of interest, as well as the detection of (presence or absence) of highly pathogenic and lethal bacterial species, or the detection of new, previously unknown, bacterial. The invention provides, for example, information on the total of bacteria in any given sample. Because of the nature of the technology, many unidentified bacteria are amplified. Thus, when testing clinical samples, new bacterial species are found which could not be identified until now from unknown bacterial populations.

Furthermore, the invention provides analysis of bacterial populations to provide a method for Quality Control. For example, in all sewage treatment plants, bacteria are used in the process of cleaning waste water. The nature of bacteria present in these systems needs to be verified for many reasons. As such, the analysis of the quality and composition of the bacteria present in these systems should be checked on a regular basis. Second, the resulting water needs to be verified as well. Both checks are currently performed using 'classical' methods, amongst which are culturing under different conditions. The invention provides a rapid, and improved technology for Quality Control of the whole process. A further advantage of the invention is, that known pathological bacteria (e.g. *legionella, salmonella* spp.) can be identified in the same process of testing the sample with a method according to the invention.

In another example, the invention provides a method for testing the disease or health status of livestock, such as broilers. The bacterial flora in the intestinal tract of broilers is influenced by the composition of feed. During the growth of broilers, generally at two or more occasions, differences are provided in the composition of the feed. This is done to optimize the ratio between feed-intake and growth. Due to the change in feed, the bacterial populations in the intestinal tract are influenced as well. Analysis of the bacterial patterns according to the invention will show the differences due to the changes in feeding.

In another example, the invention provides a method comprising germ counts. Culturing of bacterial populations is performed for many purposes and in many research projects. However, it is current practice that only particular groups of bacteria are visualized or identified (e.g. all coliformes in one group). The present invention is quantitative (when so desired), and can replace the existing use of culturing bacteria. Also, on many occasions, diseases in the intestinal tract are hard to identify. The present invention provides for the analysis, which analysis of the total bacterial contents in any organ or tissue can be performed in a rapid, reliable fashion, and thus be helpful in diagnosis of disease of man and animal alike.

Yet another example comprises use of the present invention in food technology. In the process of the preparation of food, or in the quality control of raw or fermented products such as sausages or cheese, it is essential that the same product is manufactured at a constant level. The invention provides a method enabling the detection of bacterial, viral or fungal species, allowing the verification of manufacturing conditions in the same procedure.

Generally, the sample will have to be pretreated, e.g., homogenised in order to make the nucleic acid accessible for amplification. The sample may be taken from any vertebrate having an intestinal tract and a bacterial flora therein. However, mammals and birds are preferred subjects of the present invention. Especially preferred subjects are humans and domestic animals, and in particular, cattle, poultry and other livestock. Amplification of nucleic acid should be selective in that the choice of primers should be such that a representative amplificate of all or at least a representative number of micro-organisms present in the intestinal flora is obtained. If the primers are well chosen the further details of the amplification technique employed are less critical, so that any amplification method can be used, although PCR is preferred. The length of the primers and the amplification conditions can be determined by the person skilled in the art, depending on the sample, the kind of animal, the need for specificity, etc. Typically, primers will vary in length between 20 and 30 nucleotides, and typically will be directed to a nucleic acid sequence which is present in the selected micro-organisms present in the intestinal flora of the subjects to be sampled, such as 16S rRNA and 23S rRNA.

In some cases, a nested PCR may be useful.

The amplificate itself typically will not give sufficient specific fragments so that a good analysis of the frequency/presence/absence etc. of the respective micro-organisms can be obtained. Therefore, it is important to further differentiate the nucleic acids obtained from the respective micro-organisms by subjecting them to a treatment with a number of restriction enzymes. In that manner, patterns will be obtained which contain sufficient information to enable a good analysis of flora richness, evenness, relative abundance, and amounts, revealing the state of the intestinal flora. This will certainly be very easy in the case where it is not necessary to identify particular micro-organisms, and where it suffices to compare obtained patterns with known patterns of healthy individuals (preferably obtained from an average of the patterns of many healthy individuals with certainty intervals also given). The restriction enzymes should be selected such that fragments giving relevant information are obtained. The skilled person is capable of designing a set of restriction enzymes capable of doing just that. Typically, the enzymes should recognize sequences of 4–8 basepairs, which enables selective digestion to enhance the information present in the amplificate. Typically, at least 10 different enzymes are used, but usually no more than 4 enzymes are necessary. Examples of useful restriction enzymes include, but are not limited to, CfoI and HaeIII.

The analysis of the restricted amplificate can be done in any manner capable of distinguishing between sizes of nucleic acids, in particular DNA fragments. The person skilled in the art is capable of selecting a method best fitted for his purposes. In the case of many samples having to be analyzed some kind of automated system is of course preferred. Good examples of methods for automated analysis systems require possibilities to separate and quantitate DNA fragments. For instance, for the ABI Prism (Perkin Elmer) is suitable for the present invention. In order to analyze the pattern according to the invention, it is preferred to compare the result of amplification and restriction of the sample with at least one reference sample. Some reference should be available for comparing a present state (equilibrium) of a certain animal with a healthy state (equilibrium) of the same animal, another animal, or preferably a group of animals known to be generally healthy. The more information present about the healthy state, the easier it becomes to see difference between healthy intestinal floras and floras related to pathological conditions or general health problems. Of course, the comparison is most reliable when samples are taken in the same manner under similar, if not the same, circumstances. It will often not be necessary to make direct comparisons between samples, as it will generally suffice to compare some kind of test result (numbers, barcodes, graphs, patterns and the like).

Standardizing the picture of bacterial flora can be done, e.g., in the following manner.

To enable interpretation of samples for various purposes, a baseline is established of the intestinal tract of poultry and faecal material of pigs.

The choice of animals used for the baseline is depending on a) age,
b) housing,
c) feed(intake),
d) breeding line,
e) clinical health, and
f) sex.

The most important aspect is the comparability of the samples constituting the baseline and the sample to be tested. Thus calibration is needed for at least some of the parameters given above.

An easy way of obtaining a number of references is subjecting pure bacterial cultures (of a bacterium of which it is known that it is present in the intestinal flora) to amplification and restriction in the same manner as sample will be treated. The presence and/or abundance of these bacteria in intestinal tracts can be determined based on the presence or absence of (a number of) characteristic peaks.

The invention also provides a method of flora analysis comprising determining the relative abundance of microorganisms included in said intestinal flora, or even determining simply whether a pattern is within a healthy variation of patterns without even knowing much about the constituting bacteria. This can be done once a collection of healthy patterns is available. Thus, one merely measures the relative abundance and presence/absence of peaks known to be present in the floras of healthy individuals, without knowing from which organisms said peaks originate.

Of course, the earlier mentioned pure bacteria cultures give the possibility to identify which peaks belong to which micro-organism if so desired. Of such peaks, the height and/or the area under the peak, especially in comparison with other known peaks, is a measure for the amount of a certain micro-organism present in a sample. Thus, the invention also provides a method, wherein the analysis involves determining the amount of at least one micro-organism present in said intestinal flora. In another embodiment, the invention provides a diagnostic testkit for performing a method according to the invention, the testkit comprising primers for amplification, restriction enzymes for digestion and optionally at least one reference sample comprising material derived from at least one pure bacterial culture. Preferably such a testkit comprises at least one reference pattern as described herein before.

Suitable primers to include in a testkit according to the invention are primers derived from aligned sequences. This sequence information enables the selection of homologues sequences from which primers can be developed. Preferably, primers are chosen from ribosomal RNA sequences. Preferably, at least one primer comprises the sequence 5'-AGAGTTTGATCCTGGCTCAG-3' (SEQ ID NO:1), or a functional fragment and/or derivative thereof. A functional derivative or fragment is a primer having a sequence which basepairs with the sequence with which the original sequence basepairs, or with a sequence very closely in the vicinity of the original sequence, so that the same or similar nucleic acids are obtained after amplification.

Another preferred primer comprises the sequence 5'-CCGTCAATTCCTTTRAGTTT-3'(SEQ ID NO:2), or a functional fragment and/or derivative thereof.

The invention also provides the use of a testkit according to the invention for determining presence or absence of equilibrium in intestinal bacterial flora as explained hereinbefore. The invention also provides the method for determining presence or absence of equilibrium in intestinal bacterial flora.

The term 'intestinal flora' as used herein means flora present in the digestive tract, such as the intestinal tract, the stomach, the oesophagus, the mouth or beak or other parts of, or parts close in relation to, the digestive track. Thus, intestinal flora samples may be taken from any part of, or any part close in relation to, the digestive tract.

The means and methods of the invention are in general suited for the analysis of a microbiological sample suspected of containing a variety of different microbiological organisms. An example of a microbiological organism is any kind of bacterium, phage, virus, fungus or yeast. A sample of microbiological flora can be obtained from any source suspected of containing a variety of microorganisms, preferably said sample is obtained from the digestive tract, and most preferably from the intestinal tract. It is also clear to the person skilled in the art that the means and methods of the invention may also be used to determine and/or trace the kind of plant and mammal material in nucleic acid-containing foods. It is clear to the person skilled in the art that the disclosed methods and means are not limited to intestinal tract bacterial flora, but are indeed suited for the typing of microbiological flora from many different sources, such as food samples, food additives, waste material, soils etc. With the term 'flora' is meant a collection of microbiological organisms. With the term 'bacterial flora' is meant a flora present in, obtained from or derived from the digestive tract, preferably the intestinal tract.

The invention will be explained in more detail in the following experimental part.

MATERIAL AND METHODS

Sampling

Part of the intestinal tract where isolated/obtained during post mortem examination.

In poultry, e.g., a well-defined part of the ileum between the exit of the pancreatic duct and the Mickel's Diverticulun was used.

Endoscopial investigation is used to collect samples from particular parts of the intestinal tract from live subjects feces were obtained from live subjects.

Conservation and Transport

Samples were put and maintained on dry ice immediately after collection and transported to the laboratory.

Upon arrival at the laboratory, samples were stored at −20° C.

Materials

Lysisbuffer DNA-extraction (pH 6,4)
- 142,5 g GuSCN
- 4,8 g TRIS
- 1,63 g EDTA
- Aqua ad 200 ml Wash-solution DNA-extraction (pH 6.4)
- 142,5 g GuSCN
- 4,8 g TRIS
- Aqua ad 200 ml)

DE-solution DNA-extraction
- 0.75 ml HCL 35%
- 10 g Diatomaceous Earth
- Aqua ad 50 ml Sample Preparation 1. Sample handling
   a. intestinal tract Approximately 2 cm of the specified location was sliced lengthwise using a scalpel. The entire contents were transferred into a sterile tube.

b. endoscopial biopsies and fecal material

Samples were transferred into sterile tubes.

2. Homogenization

Mixing by manually shaking was performed until the substance was visually homogenous.

3. DNA-extraction
   a. Quantity

Approximately 0.2 g of homogeneous material was used. In cases of watery samples, a volume of approximately 250 µl was used.

b. DNA-extraction

The DNA-extraction was performed generally according to Boom's method.

One ml of lysisbuffer was added to the homogenous sample. The suspension was vortexed for 30 seconds, and placed at room temperature for one hour.

The suspension was centrifuged at 15000–17000 g for 20 seconds.

The supernatant was transferred to a sterile tube containing 50 µl of DE-solution. The suspension was vortexed for 30 seconds, and centrifugation at 15000–17000 g for 20 seconds.

After removal of the supernatant, five washing steps were performed:
1. 200 µl wash-solution,
2. 200 µl wash-solution,
3. 200 µl 70% Ethanol,
4. 200 µl 70% Ethanol,
5. 200 µl Aceton p.a..

The pellet was air-dried for 15 minutes at 56° C.

The pellet was resuspended in 75 µl ddH2O (overnight 37° C.).

Finally, the supernatant was transferred to a new eppendorf cup and stored at 4° C.

PCR

Polymerase Chain Reaction was performed using 1,5 ul DNA in a total reaction volume of 15 µl, containing amplitaq DNA polymerase (0.07 unit/µl), primers (1.3 mM of forward and reverse primer), dNTPs (200 mM) and 60 mM KCl, 12 mM HCl pH 8,3 and 1,8 mM MgCl2.

Primer sequences:
Forward 5'-AGAGTTTGATCCTGGCTCAG-3' (SEQ ID NO:1) Label FAM
Reverse 5'-CCGTCAATTCCTTTRAGTTT-3' (SEQ ID NO:2), Label TET PCR programme:

| 1 cycle of | 5 min 95° C. |
|---|---|
| 35 cycles of | 30 sec 95° C. |
|  | 45 sec 56° C. |
|  | 2 min 72° C. |
| 1 cycle of | 5 min 72° C. |

Both primers were labelled with fluorescent probes to enable automated analysis.

The purpose of this reaction is an amplification of as many bacterial organisms as possible. This generally results in about 50 fragments.

Restriction

Restriction digestion was performed on the PCR-products with different restriction enzymes, such as

| HaeIII | GG'CC, |
|---|---|
| CfoI (= HhaI) | GCG'C, |
| TaqI | T'CGA, |
| HinfI | G'ANTC, |
| MspI | C'CGG, |
| PstI | CTGCA'G, and |
| HindIII | A'AGCTT. |

Analysis

Size analysis of the DNA-fragments was performed on an ABI 377 DNA Sequencer using fluorescently labelled primers. The conditions of the tun on the ABI377 Prism Sequencing system were as follows: ABI Collection software version 2.1 with well-to-read distance 36 cm; running conditions 3000 V, 60 mA, 200 W, collection time 5 hours.

Size-analysis was performed using ABI-software. Lanetracking, Genotyper, Data analysis was performing using GeneScan 3.1 and Genotyper 2.0 software according to the manufacturer's instructions.

Pure Culture Bacteria

Several bacterial strains, e.g., *Clostridium perfringens, Staphylococcus aureus, Mycoplasma gallisepticum, Mycoplasma Synovium, Ornitobacter rhinotracheale, Escherichia coli,* Lactobacilliae, Enterococcae and *Pseudomonas aeruginosa,* were used as references.

Polymerase Chain Reaction as described previously is carried out on pure cultured bacteria. The size of the PCR-product is specific for each bacterium.

Restriction enzymes can be used to identify a number of fragments.

The overall picture of fragments after the PCR and after the use of restriction enzymes results in a 'pattern' of a pure culture. This pattern can be identified in any intestinal sample depending on the amount of bacteria present.

Interpretation

1. Richness

The results of the analysis are visualized in a figure, showing peaks corresponding to the size of the DNA-fragments.

These peaks generally are related to bacterial species. The number of peaks identified is a indication for the total number of bacterial species. Using information from pure cultured bacteria, this also provides information on the presence or absence of specific bacteria.

2. Evenness

Furthermore, the peaks provide information on the relative quantity of each DNA-fragment. The ratio of the DNA-fragments based on peak-height and peak-area can be used to estimate the number of certain bacteria present in the sample.

Polymerase chain reaction as described before is carried out after DNA extraction from pure cultured bacterial. Thus, samples can be interpreted to see whether some bacteria are overwhelmingly present or almost absent.

BRIEF DESCRIPTION OF THE FIGURES

Figures are enclosed as illustration of some of the possible situations. FIG. 1 shows DNA-fragments with sizes ranging from 100 to 900 basepairs, whereas FIG. 2 shows DNA-fragments between 300 and 600 basepairs. Each peak in the figures represents a specific DNA-fragment.

The DNA-fragment for three individual chickens were based on samples from the duodenum. Two samples were derived from clinically "healthy" individuals (A and B), whereas one sample represents a 'non-healthy' individual (C). The "non-healthy" individual showed one major additional DNA-fragment (marked "Additional") which was not present in two "healthy" individuals.

Figure 1:
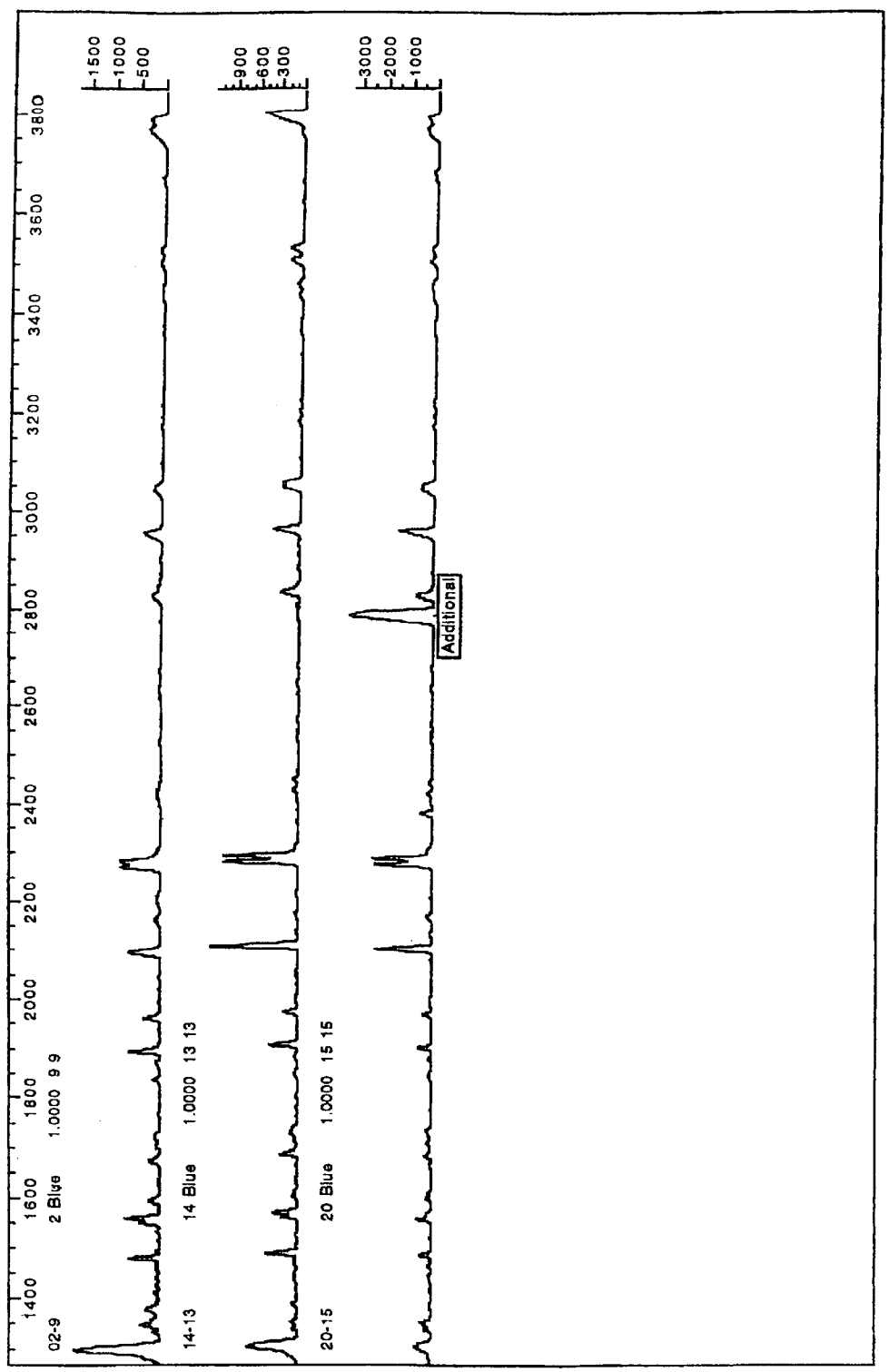
FIGS. 1 and 2 represent the DNA-patterns of three microbiological populations obtained from three individuals.
Figure 2:
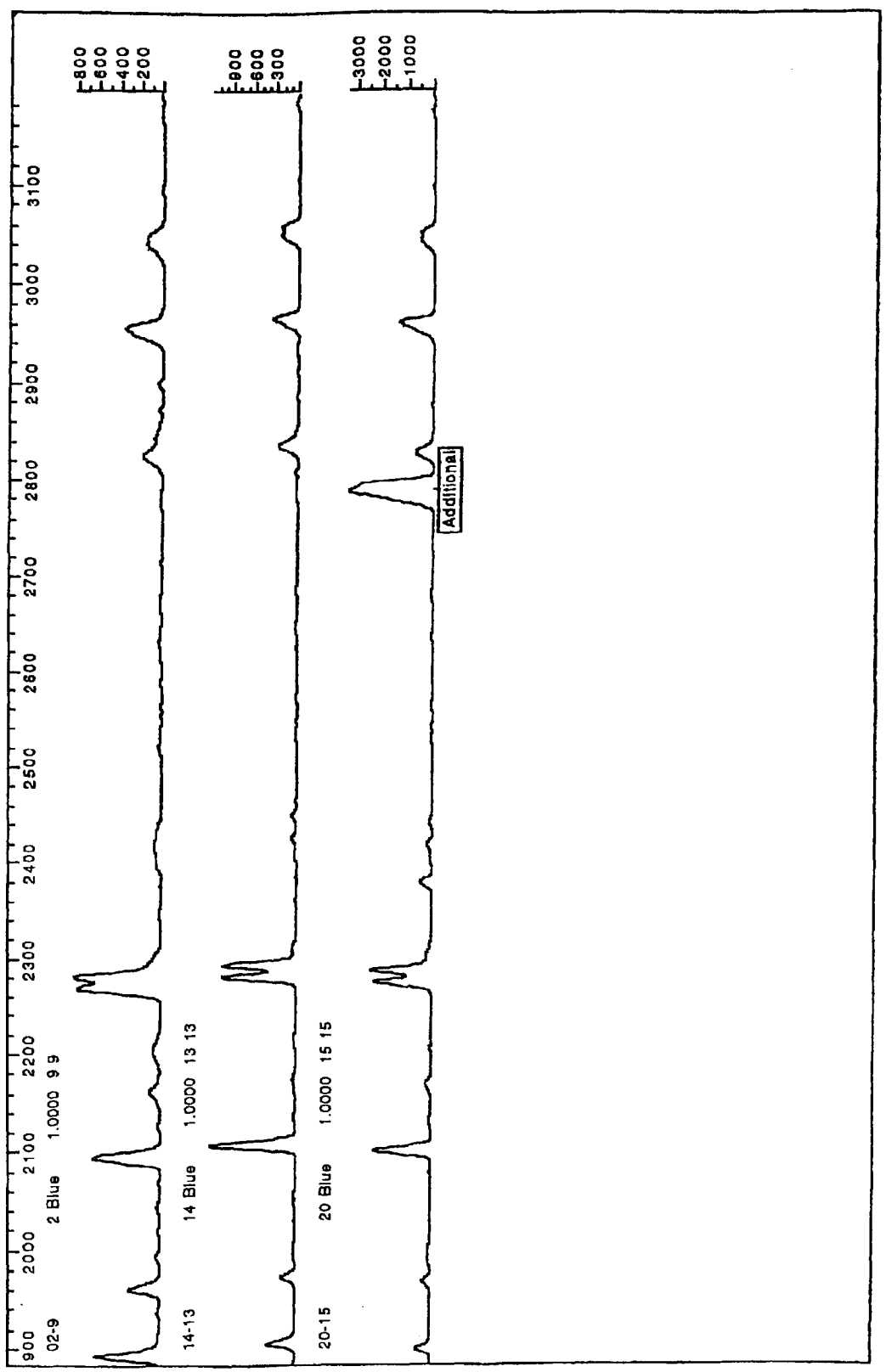
Figure 3:
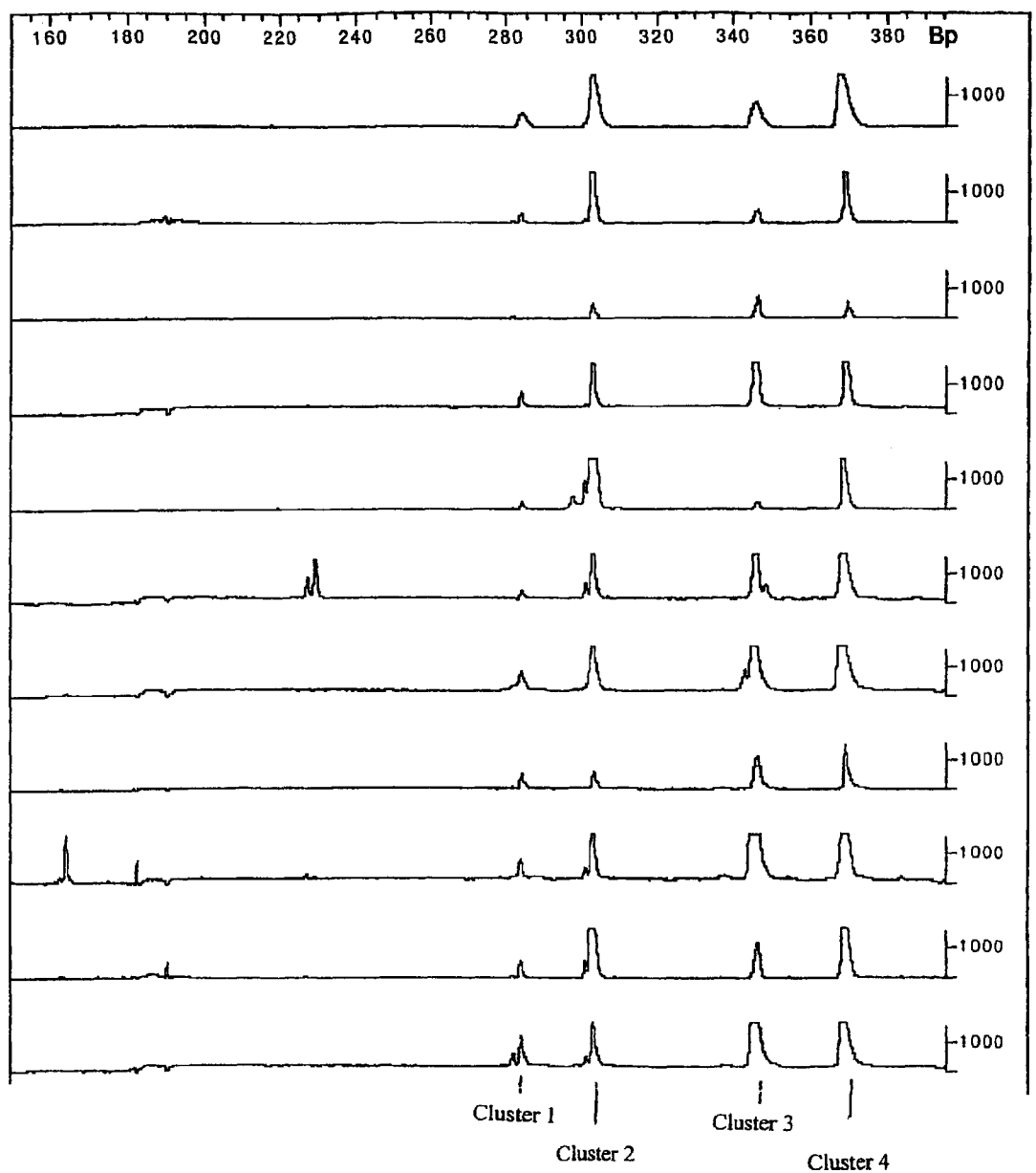
Figure 4:
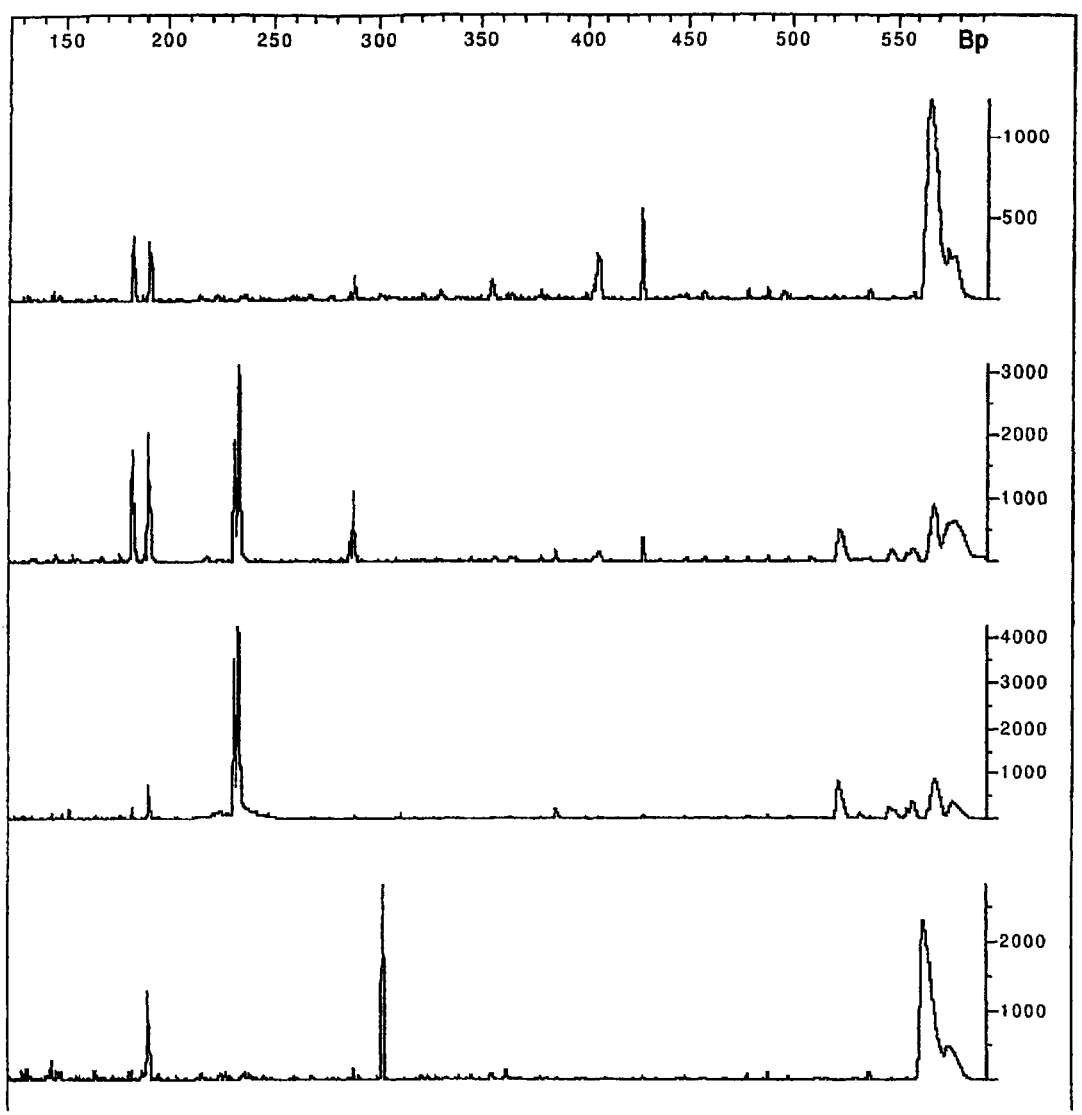

FIGS. 3 and 4 illustrate part of a procedure to test for bacterial overgrowth in broilers. Illustrations show that under distinct disease conditions, samples exhibit the same clusters, whereas bacterial variation can easily be identified with our technology.

Bacterial clusters, or species are identified through DNA-fragment size, using base pairs.

FIG. 3. A total of eleven samples are shown. Each sample is based on a specimen from the intestinal tract form clinically healthy chicken at 3,5 weeks of age.

At lest four major bacterial clusters are present, with a few other bacterial species present in some of the samples as well. Two issues are herewith illustrated:

A. Major clusters are present in all samples,

B. The relative number of bacteria present is different in the samples.

FIG. 4. A total of four samples are shown. Each sample is known to exhibit large differences at common bacterial/germ counts.

Two issues are illustrated here.

A. Our procedure is clearly capable of identifying similar, large, differences as detected in the germ counts. Samples with high counts for specific groups in the germ counts show identical DNA-fragments, whereas these fragments are not present in the samples without these specific bacteria.

B. This new technology is identifying additional information compared to the "Classical" germ counts, because our methods are including all bacterial species in one analysis. Even unknown bacteria are included.

---

---

What is claimed is:

1. A method for analyzing the composition of a microbiological flora comprising more than one species of microorganism, said method comprising:

providing a sample of said microbiological flora;

amplifying nucleic acid from the more than one species of microorganism presented in said sample to produce an amplificate;

subjecting the amplificate after amplification to at least one restriction digestion to produce restriction fragments from the more than one species of microorganism;

preparing a resulting pattern based on the restriction fragments of the more than one species of microorganism in the sample; and comparing the resulting pattern of the sample with at least one reference pattern to determine if the sample of microbiological flora is in equilibrium with the at least one reference pattern.

2. The method according to claim 1, wherein said microbiological flora is bacterial flora.

3. The method according to claim 1, wherein said flora is derived from the digestive tract.

4. The method according to claim 1, wherein said reference pattern is derived from another source.

5. The method according to claim 1, further comprising analyzing the resulting pattern of restriction fragments to determine the relative abundance of micro-organisms included in flora.

6. A method to determine the relative ratios of microorganisms present in a microbiological flora, said method comprising:

providing a sample of said microbiological flora;

amplifying nucleic acid from the more than one species of microorganism present in said sample to produce an amplificate;

subjecting the amplificate after amplification to at least one restriction digestion to produce restriction fragments from the more than one species of microorganism;

preparing a resulting pattern based on the restriction fragments of the more than one species of microorganism in the sample; and analyzing the resulting pattern of restriction fragments to determine the relative ratios of microorganism present in said flora.

7. A kit for performing the method of claim 1 comprising:

two primers for amplification of nucleic acids in a microbiological flora sample comprising more than one species of microorganism to produce an amplificate, wherein at least one of said primers comprise the sequence 5'-AGAGTTTGATCCTGGTCAG-3' (SEQ ID NO.1);

at least two restriction enzymes for digestion of an amplificate of a microbiological flora sample to produce restriction fragments from more than one species of microorganism; and at least one reference pattern of flora for comparative analysis of a resulting pattern of the restriction fragments from the digestion of the microbiological flora sample, wherein said at least one reference pattern of flora is selected from microorganisms found in intestinal flora.

8. The kit of claim 7, wherein at least one of said primers comprise the sequence 5'-AGAGTTTGATCCTGGCTCAG-3' (SEQ ID NO:1).

9. A kit for analyzing the composition of microbiological flora comprising more than one species of microorganisms, the kit comprising:

two primers for amplification of nucleic acids in a microbiological flora sample comprising more than one species of microorganisms to produce an amplificate, and at least two restriction enzymes for digestion of the amplificate of the microbiological flora sample to produce restriction fragments from the more than one species of microorganisms; and wherein at least one of said primers comprise the sequence 5'-CCGTCAATTCCTTTRAGTTT-3' (SEQ ID NO:2).

10. A method of using the kit according to claim 7 for determining presence or absence of equilibrium in intestinal bacterial flora.

11. The method according to claim 1, wherein said providing a sample comprises obtaining a sample from feces of a subject.

12. The method according to claim 1, wherein said providing a sample comprises obtaining the sample from a broiler.

13. The method according to claim 1, wherein said providing a sample comprises obtained a sample from a tissue or organ of a subject, and further comprising analyzing the total bacterial content of said tissue or organ.

14. The method of claim 1, wherein said reference pattern is a standardized baseline pattern derived from a plurality of subjects with healthy flora.

15. The method of claim 1, wherein said subjecting the amplificate to restriction digestion comprises subjecting the amplificate to restriction enzymes recognizing nucleotide sequences of about 4 to about 8 nucleotides.

16. A method of analyzing the composition of a bacterial flora, comprising:

obtaining a sample of bacterial flora derived from a digestive tract of a subject;

amplifying nucleic acid from more than one species of bacteria presented in said samples with at least one primer of about 20 to 30 nucleotides directed to a nucleic acid believed to be present in said sample to produce an amplificate;

subjecting the amplificate after amplification to restriction digestion;

analyzing a resulting pattern of restriction fragments by comparing a restriction pattern of the sample with at least one reference restriction pattern; and determining relative abundance and relative ratios of said bacterial flora.

17. A method for analyzing the composition of a bacterial flora, comprising:

obtaining a sample of bacterial flora derived from a digestive tract of a subject;

amplifying nucleic acid from more than one species of bacteria presented in said sample with at least one primer of about 20 to 30 nucleotides directed to a nucleic acid believed to be present in said sample to produce an amplificate;

subjecting the amplificate after amplification to restriction digestion;

determining presence or absence of equilibrium in intestinal bacterial flora by comparing a restriction pattern of the amplificate to at least one reference restriction pattern; and determining relative abundance and relative ratios of said bacterial flora.

18. The method according to claim 1 wherein said reference pattern is used for determining differences or similarities with said sample of microbiological flora.

* * * * *

UNITED STATES PATENT AND TRADEMARK OFFICE
CERTIFICATE OF CORRECTION

PATENT NO.     : 6,495,325 B1
DATED          : December 17, 2002
INVENTOR(S)    : Hendrick van Haeringen and Willem Anne van Haeringen It is certified that error appears in the above-identified patent and that said Letters Patent is hereby corrected as shown below:

<u>Title page,</u>
Item [75], Inventors, change "Anne" to -- A. --

<u>Column 5,</u>
Line 3, after "instance," delete "for"

<u>Column 6,</u>
Line 29, change "oesophagus" to -- esophagus --
Line 60, change "where" to -- were --
Line 66, change "subjects feces" to -- subjects. Feces --

<u>Column 8,</u>
Line 40, change "performing" to -- performed --

<u>Column 9,</u>
Line 51, change "non-healthy'" to -- "non-healthy" --

<u>Column 12,</u>
Line 11, change "obtained" to -- obtaining --
Line 26, change "samples" to -- sample --

Signed and Sealed this

Twentieth Day of May, 2003

JAMES E. ROGAN
*Director of the United States Patent and Trademark Office*

SEQUENCE LISTING

```
<160> NUMBER OF SEQ ID NOS: 2

<210> SEQ ID NO 1
<211> LENGTH: 20
<212> TYPE: DNA
<213> ORGANISM: Unknown
<220> FEATURE:
<223> OTHER INFORMATION: Primer

<400> SEQUENCE: 1
agagtttgat cctggctcag                                                    20

<210> SEQ ID NO 2
<211> LENGTH: 20
<212> TYPE: DNA
<213> ORGANISM: Unknown
<220> FEATURE:
<223> OTHER INFORMATION: Primer

<400> SEQUENCE: 2
ccgtcaattc ctttragttt                                                    20
```